(12) United States Patent
Balachandran et al.

(10) Patent No.: US 11,414,093 B2
(45) Date of Patent: Aug. 16, 2022

(54) SYSTEM AND METHOD FOR TRANSITIONING A VEHICLE FROM AN AUTONOMOUS MODE IN RESPONSE TO A HANDOVER EVENT

(71) Applicant: Toyota Research Institute, Inc., Los Altos, CA (US)

(72) Inventors: Avinash Balachandran, Sunnyvale, CA (US); Carrie Bobier-Tiu, Sunnyvale, CA (US)

(73) Assignee: Toyota Research Institute, Inc., Los Altos, CA (US)

( * ) Notice: Subject to any disclaimer, the term of this patent is extended or adjusted under 35 U.S.C. 154(b) by 363 days.

(21) Appl. No.: 16/556,558

(22) Filed: Aug. 30, 2019

(65) Prior Publication Data
US 2021/0061298 A1 Mar. 4, 2021

(51) Int. Cl.
*B60W 50/08* (2020.01)
*B60W 30/02* (2012.01)
(Continued)

(52) U.S. Cl.
CPC .............. *B60W 50/08* (2013.01); *A61B 5/01* (2013.01); *A61B 5/02055* (2013.01); *A61B 5/11* (2013.01); *A61B 5/14551* (2013.01); *A61B 5/163* (2017.08); *A61B 5/18* (2013.01); *A61B 5/4266* (2013.01); *B60W 30/025* (2013.01); *B60W 30/18* (2013.01); *A61B 5/021* (2013.01);
(Continued)

(58) Field of Classification Search
CPC .... B60W 50/08; B60W 30/025; B60W 30/18; B60W 2556/00; B60W 2050/0071; B60W 2720/106; B60W 2050/0088; B60W 2540/221; B60W 2540/30; B60W 2050/0096; B60W 2420/42; B60W 2720/10; B60W 2556/10; B60W 2050/0075; B60W 60/0054; A61B 5/02055; A61B 5/01; A61B 5/14551; A61B 5/11; A61B 5/163; A61B 5/18; A61B 5/4266; A61B 5/021; A61B 5/024; A61B 5/0816; A61B 5/745; B60Y 2302/05

See application file for complete search history.

(56) References Cited

U.S. PATENT DOCUMENTS 9,235,211 B2 1/2016 Davidsson et al.
9,703,289 B2 7/2017 Sato et al.
(Continued)

*Primary Examiner* — Yuen Wong
(74) *Attorney, Agent, or Firm* — Christopher G. Darrow; Darrow Mustafa PC

(57) ABSTRACT

A system for transitioning a vehicle from an autonomous mode in response to a handover event, the system includes one or more processors and a memory device operably coupled with the one or more processors. The memory device stores a driver assessment module, an operational condition adjustment module, and a transitioning module. The driver assessment module configures the one or more processors to determine an ability level and a comfort level of a driver of the vehicle in response to the handover event. The operational condition adjustment module configures the one or more to adjust at least one operating condition of the vehicle to be within the ability level of the driver and comfort level. The transitioning module configures the one or more processors to transition the vehicle from the autonomous mode to a driver input mode.

20 Claims, 4 Drawing Sheets

(51) Int. Cl.
*A61B 5/0205* (2006.01)
*A61B 5/01* (2006.01)
*A61B 5/1455* (2006.01)
*A61B 5/11* (2006.01)
*A61B 5/16* (2006.01)
*A61B 5/18* (2006.01)
*A61B 5/00* (2006.01)
*B60W 30/18* (2012.01)
*A61B 5/021* (2006.01)
*B60W 50/00* (2006.01)
*A61B 5/024* (2006.01)
*A61B 5/08* (2006.01)

(52) U.S. Cl.
CPC ............. *A61B 5/024* (2013.01); *A61B 5/0816* (2013.01); *B60W 2050/0071* (2013.01); *B60W 2556/00* (2020.02); *B60W 2720/106* (2013.01)

(56) References Cited

U.S. PATENT DOCUMENTS

| | | |
|---|---|---|
| 9,834,224 B2 | 12/2017 | Gordon et al. |
| 10,232,861 B2 | 3/2019 | Huang et al. |
| 2017/0066452 A1 | 3/2017 | Scofield |
| 2017/0368936 A1 | 12/2017 | Kojima |
| 2018/0088574 A1 | 3/2018 | Latotzki et al. |
| 2018/0101170 A1* | 4/2018 | Cawley ............... G05D 1/0061 |
| 2018/0284764 A1* | 10/2018 | Asghar ............... G05D 1/0088 |

* cited by examiner

SYSTEM AND METHOD FOR TRANSITIONING A VEHICLE FROM AN AUTONOMOUS MODE IN RESPONSE TO A HANDOVER EVENT

TECHNICAL FIELD

The subject matter described herein relates, in general, to systems and methods for transitioning a vehicle from an autonomous mode in response to a handover event.

BACKGROUND

The background description provided is to present the context of the disclosure generally. Work of the inventor, to the extent it may be described in this background section, and aspects of the description that may not otherwise qualify as prior art at the time of filing, are neither expressly nor impliedly admitted as prior art against the present technology.

Some current vehicles can sense the environment around the vehicle and move safely with little or no driver input. These types of vehicles are commonly referred to as autonomous vehicles. However, the level of autonomy for an autonomous vehicle may vary. In some cases, an autonomous vehicle can operate without any driver input. However, in other cases, the autonomous vehicle may need driver input.

The need for driver input may occur in situations wherein one or more sensors or electronic systems of the autonomous vehicle either fail or have difficulty sensing the environment around the autonomous vehicle due to external causes. In other situations, the autonomous vehicle may not have the ability to operate itself in certain locations. For example, some autonomous vehicles can operate themselves on major roadways, such as expressways, but have limited or reduced capabilities to operate themselves on lesser-used roadways, such as residential streets, driveways, and seldom-used roads. In these types of situations, the autonomous vehicle may need to handover some or all operations of the vehicle to the driver.

SUMMARY

This section generally summarizes the disclosure and is not a comprehensive explanation of its full scope or all its features.

A system for transitioning a vehicle from an autonomous mode in response to a handover event includes one or more processors and a memory device operably coupled with the one or more processors. The memory device stores a driver assessment module, an operational condition adjustment module, and a transitioning module. The driver assessment module configures the one or more processors to determine an ability level and a comfort level of a driver of the vehicle. The comfort level of the driver may be based on a learned physiological condition of the driver determined by observing one or more physiological conditions of the driver when the driver operates the vehicle in the driver input mode. The ability level of the driver may be based on an outer limit of the ability of the driver to operate the vehicle in the driver input mode. In addition to physiological based information, the comfort level can be learned from vehicle data with the need for physiological data. In particular, the comfort level may be determined by statistically observing a particular driver's vehicle data over time and determine what they are comfortable with using machine learning and some statistical inference.

The operational condition adjustment module configures the one or more processors to adjust at least one operating condition of the vehicle to be within the ability level and comfort level of the driver in response to the handover event. The transitioning module configures the one or more processors to transition the vehicle from the autonomous mode to a driver input mode after the operating condition of the vehicle has been adjusted to be within the ability level of the driver and the comfort level of the driver.

A method for transitioning a vehicle from an autonomous mode in response to a handover event includes the steps of determining an ability level and a comfort level of a driver of the vehicle, adjusting at least one operating condition of the vehicle to be within the ability level and comfort level of the driver in response to the handover event, and transitioning the vehicle from the autonomous mode to a driver input mode after the operating condition of the vehicle has been adjusted to be within the ability level of the driver and the comfort level of the driver. The comfort level of the driver may be based on a learned physiological condition of the driver determined by observing one or more physiological conditions of the driver when the driver operates the vehicle in the driver input mode. The ability level of the driver may be based on an outer limit of the ability of the driver to operate the vehicle in the driver input mode.

A non-transitory computer-readable medium for transitioning a vehicle from an autonomous mode in response to a handover event includes instructions that when executed by one or more processors cause the one or more processors to determine an ability level and a comfort level of a driver of the vehicle, adjust at least one operating condition of the vehicle to be within the ability level of the driver and comfort level, and transition the vehicle from the autonomous mode to a driver input mode after the operating condition of the vehicle has been adjusted to be within the ability level of the driver and the comfort level of the driver. The comfort level of the driver may be based on a learned physiological condition of the driver determined by observing one or more physiological conditions of the driver when the driver operates the vehicle in the driver input mode. The ability level of the driver may be based on an outer limit of the ability of the driver to operate the vehicle in the driver input mode.

Further areas of applicability and various methods of enhancing the disclosed technology will become apparent from the description provided. The description and specific examples in this summary are intended for illustration only and are not intended to limit the scope of the present disclosure.

BRIEF DESCRIPTION OF THE DRAWINGS

The accompanying drawings, which are incorporated in and constitute a part of the specification, illustrate various systems, methods, and other embodiments of the disclosure. It will be appreciated that the illustrated element boundaries (e.g., boxes, groups of boxes, or other shapes) in the figures represent one embodiment of the boundaries. In some embodiments, one element may be designed as multiple elements or multiple elements may be designed as one element. In some embodiments, an element shown as an internal component of another element may be implemented as an external component and vice versa. Furthermore, elements may not be drawn to scale.

DETAILED DESCRIPTION

Described is a system and method for transitioning a vehicle from an autonomous mode to a driver input mode in response to a handover event. A handover event may be a present or future event that will utilize the driver to provide input to the vehicle. For example, the handover event may be caused by a failure of one or more components of the vehicle, external factors impacting one or more components of the vehicle, such as adverse weather conditions, or could be any situation wherein the autonomous system of the vehicle is unable to operate the vehicle in a safe manner and therefore utilizes input from the driver.

The system and method for transitioning the vehicle from an autonomous mode to a driver input mode further considers the ability level and the comfort level of the driver. The ability level of the driver may be representative of the outer limits of the driver's ability. The comfort level of the driver may be based on physiological factors of the driver learned by observing one or more physiological factors of the driver when the driver operates the vehicle in a driver input mode. In addition to physiological based information, the comfort level can be learned from vehicle data with the need for physiological data. In particular, the comfort level may be determined by statistically observing a particular driver's vehicle data over time and determine what they are comfortable with using machine learning and some statistical inference. Depending on the ability and comfort level of the driver, the transition to the driver input mode from the autonomous mode may require changing the operating condition of the vehicle so as to match the ability and/or comfort level of the driver. In some situations, this may require slowing the vehicle down to a speed that is within the driver's ability to control the vehicle and/or comfort level and/or delaying the transition to the driver input mode so as to allow the driver to have the ability and be comfortable with taking over control of the vehicle.

Figure 1:
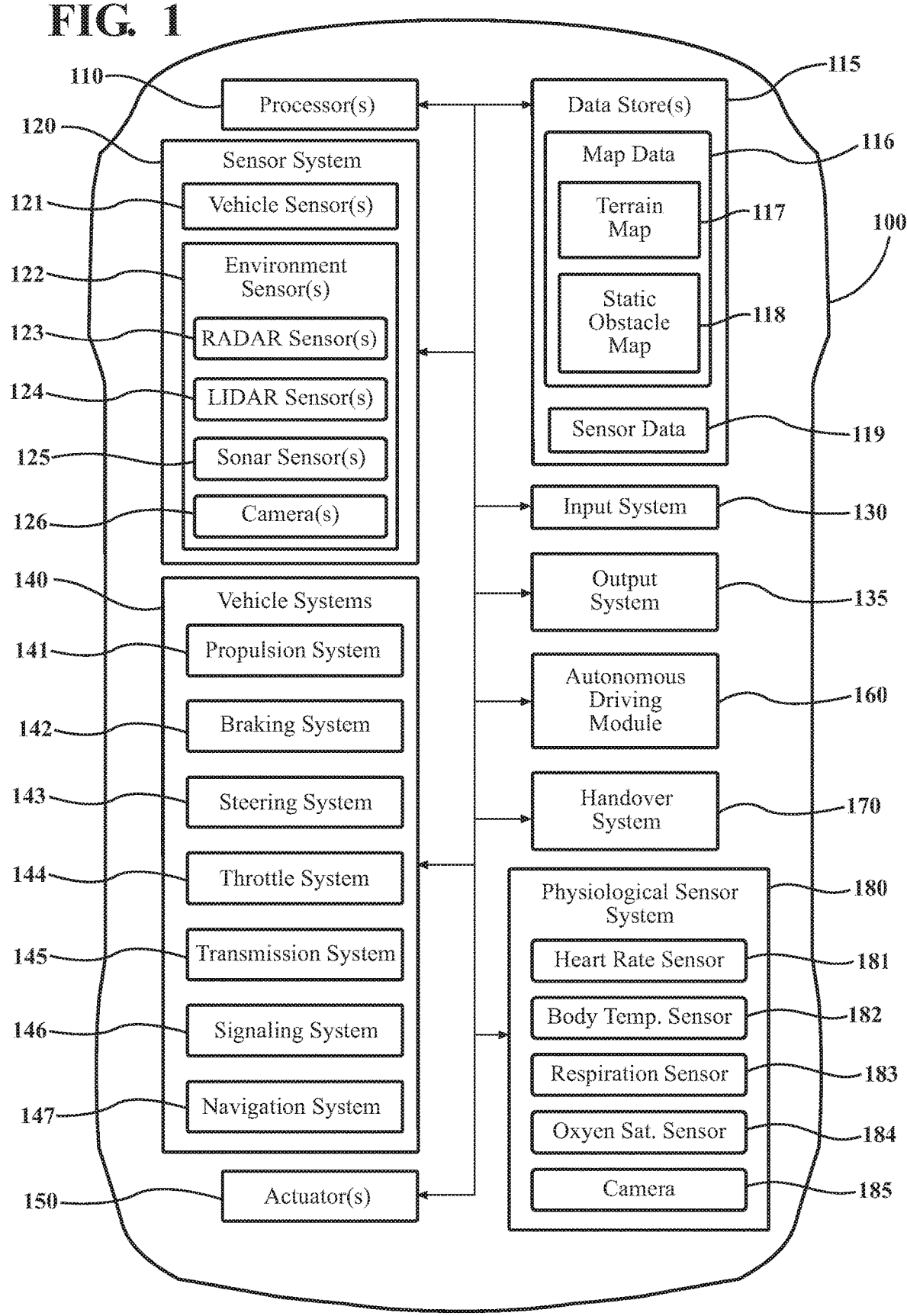
FIG. 1 illustrates one embodiment of a vehicle within which systems and methods disclosed herein may be implemented.

Referring to FIG. 1, an example of a vehicle 100 is illustrated. As used herein, a "vehicle" is any form of powered transport. In one or more implementations, the vehicle 100 is an automobile. While arrangements will be described herein with respect to automobiles, it will be understood that embodiments are not limited to automobiles. In some implementations, the vehicle 100 may be any robotic device or form of powered transport that, for example, includes one or more automated or autonomous systems, and thus benefits from the functionality discussed herein.

In various embodiments, the automated/autonomous systems or combination of systems may vary. For example, in one aspect, the automated system is a system that provides autonomous control of the vehicle according to one or more levels of automation such as the levels defined by the Society of Automotive Engineers (SAE) (e.g., levels 0-5). As such, the autonomous system may provide fully autonomous control, as discussed in relation to the autonomous driving module 160 but may also provide, in some situations, a driver input mode, where input from the driver is utilized.

As such, the vehicle 100 may operate in an autonomous mode wherein the vehicle does not require inputs from the driver but may also operate in a driver input mode in which the vehicle requires inputs from the driver in order to operate in a safe manner. The driver input mode could be a manual mode that relies entirely on the inputs of the driver or could be a semi-autonomous mode which utilizes input from the driver in combination with one or more functions from the autonomous driving module 160. As such, it should be understood that the driver input mode should be interpreted broadly and could include any mode of the vehicle wherein input from the driver is utilized to operate the vehicle.

The vehicle 100 also includes various elements. It will be understood that in various embodiments, it may not be necessary for the vehicle 100 to have all of the elements shown in FIG. 1. The vehicle 100 can have any combination of the various elements shown in FIG. 1. Further, the vehicle 100 can have additional elements to those shown in FIG. 1. In some arrangements, the vehicle 100 may be implemented without one or more of the elements shown in FIG. 1. While the various elements are shown as being located within the vehicle 100 in FIG. 1, it will be understood that one or more of these elements can be located external to the vehicle 100. Further, the elements shown may be physically separated by large distances and provided as remote services (e.g., cloud-computing services).

Some of the possible elements of the vehicle 100 are shown in FIG. 1 and will be described along with subsequent figures. However, a description of many of the elements in FIG. 1 will be provided after the discussion of FIGS. 2-4 for purposes of brevity of this description. Additionally, it will be appreciated that for simplicity and clarity of illustration, where appropriate, reference numerals have been repeated among the different figures to indicate corresponding or analogous elements. In addition, the discussion outlines numerous specific details to provide a thorough understanding of the embodiments described herein. It should be understood that the embodiments described herein may be practiced using various combinations of these elements.

In either case, the vehicle 100 includes a handover system 170. The handover system 170 may be incorporated within the autonomous driving module 160 or may be separate as shown. The handover system 170 may receive input information from any of the systems shown in FIG. 1. In particular, the handover system 170 may receive information from the sensor system 120, which includes one or more vehicle sensors 121 and environment sensors 122. In addition to the sensor system 120, the handover system 170 may also receive information from the physiological sensor system 180 which may be configured to measure a number of different physiological conditions of the driver of the vehicle 100.

The sensor system 120 can include any suitable type of sensor. Various examples of different types of sensors will be described herein. However, it will be understood that the embodiments are not limited to the particular sensors described. The sensor system 120 can include one or more vehicle sensors 121. The vehicle sensor(s) 121 can detect, determine, and/or sense information about the vehicle 100 itself. In one or more arrangements, the vehicle sensor(s) 121 can be configured to detect, and/or sense position and orientation changes of the vehicle 100, such as, for example, based on inertial acceleration. In one or more arrangements, the vehicle sensor(s) 121 can include one or more accelerometers, one or more gyroscopes, an inertial measurement unit (IMU), a dead-reckoning system, a global navigation satellite system (GNSS), a global positioning system (GPS), a navigation system 147, and/or other suitable sensors. The vehicle sensor(s) 121 can be configured to detect, and/or sense one or more characteristics of the vehicle 100. In one or more arrangements, the vehicle sensor(s) 121 can include a speedometer to determine a current speed of the vehicle 100.

Alternatively, or in addition, the sensor system 120 can include one or more environment sensors 122 configured to acquire, and/or sense driving environment data. "Driving environment data" includes data or information about the external environment in which an autonomous vehicle is located or one or more portions thereof. For example, the one or more environment sensors 122 can be configured to detect, quantify and/or sense obstacles in at least a portion of the external environment of the vehicle 100 and/or information/data about such obstacles. Such obstacles may be stationary objects and/or dynamic objects. The one or more environment sensors 122 can be configured to detect, measure, quantify and/or sense other things in the external environment of the vehicle 100, such as, for example, lane markers, signs, traffic lights, traffic signs, lane lines, crosswalks, curbs proximate the vehicle 100, off-road objects, etc.

Various examples of sensors of the sensor system 120 will be described herein. The example sensors may be part of the one or more environment sensors 122 and/or the one or more vehicle sensors 121. However, it will be understood that the embodiments are not limited to the particular sensors described.

As an example, in one or more arrangements, the sensor system 120 can include one or more radar sensors 123, one or more LIDAR sensors 124, one or more sonar sensors 125, and/or one or more cameras 126. In one or more arrangements, the one or more cameras 126 can be high dynamic range (HDR) cameras or infrared (IR) cameras.

The physiological sensor system 180 may include any one of a number of different sensors for measuring one or more physiological conditions of the driver operating the vehicle 100. For example, the physiological sensor system may include a heart rate sensor 181 that is capable of measuring the pulse of the driver as the driver operates the vehicle 100. The body temperature sensor 182 may be configured to measure the body temperature of the driver as the driver operates the vehicle 100. The respiration sensor 183 and the oxygen saturation sensor 184 may be configured to measure both the respiration of the driver of the vehicle 100 and the oxygen saturation in the blood of the driver of the vehicle 100 as the driver operates the vehicle 100.

In addition to the sensors mentioned above, the physiological sensor system 180 may include one or more cameras 185 capable of visually monitoring the driver of the vehicle 100. As such, the one or more cameras 185 can measure physiological conditions visually perceivable from the driver as the driver operates the vehicle 100. These visual physiological conditions could include perspiration, eye movements, and/or gestures of the driver operating the vehicle 100. As will be described later in this disclosure, measurements taken by the sensors making up the physiological sensor system 180 may be utilized to learn a comfort level of the driver as the driver operates the vehicle 100 in a driver input mode. In addition to physiological based information, the comfort level can be learned from vehicle data with the need for physiological data. In particular, the comfort level may be determined by statistically observing a particular driver's vehicle data over time and determine what they are comfortable with using machine learning and some statistical inference.

Figure 2:
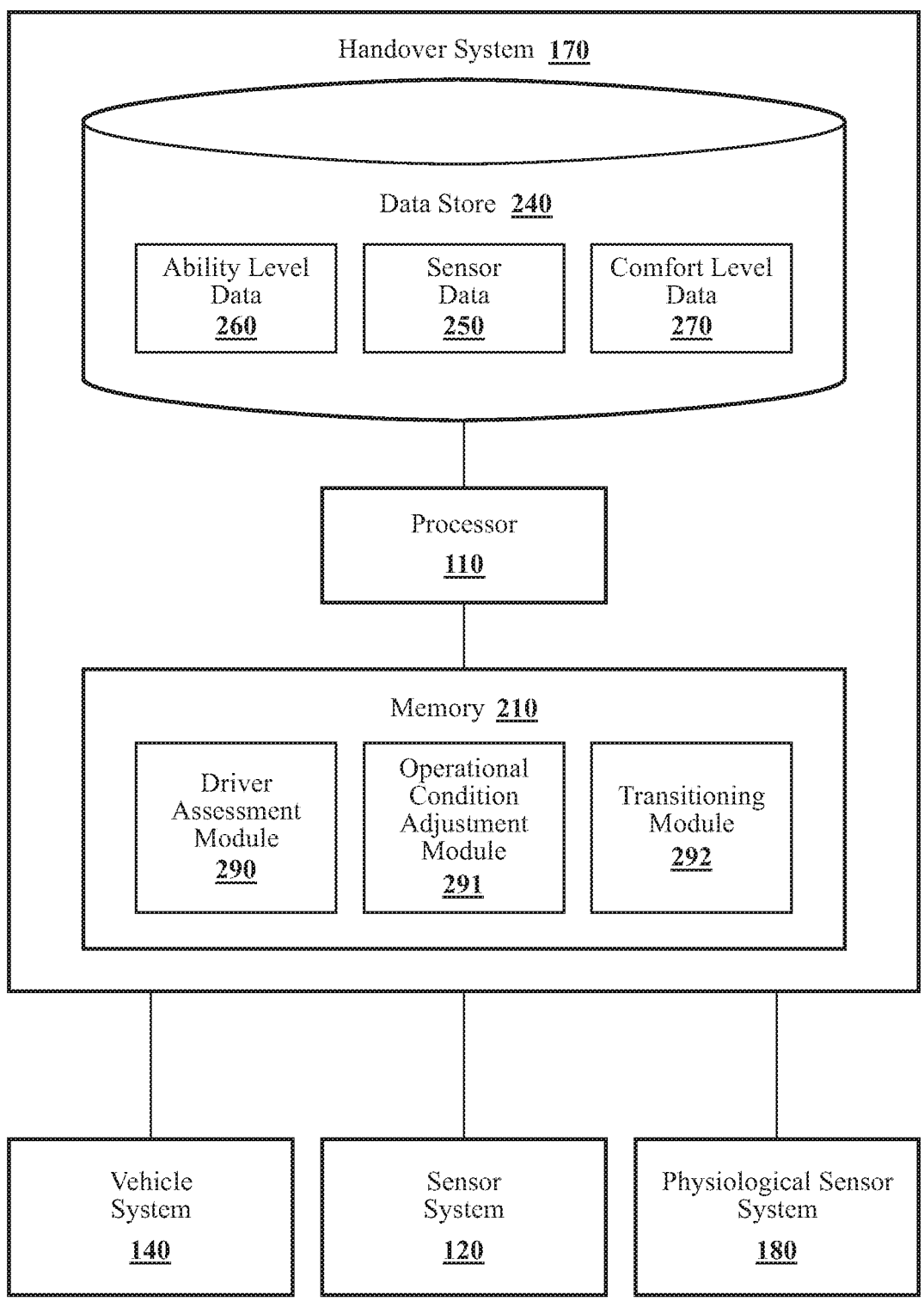
FIG. 2 illustrates one embodiment of a handover system that is associated with handing over control of a vehicle to a driver from an autonomous mode.

With reference to FIG. 2, one embodiment of the handover system 170 is further illustrated. As shown, the handover system 170 includes a processor(s) 110. Accordingly, the processor(s) 110 may be a part of the handover system 170 or the handover system 170 may access the processor(s) 110 through a data bus or another communication path. In one or more embodiments, the processor(s) 110 is an application-specific integrated circuit that is configured to implement functions associated with a driver assessment module 290, an operational condition adjustment module 291, and a transitioning module 292. In general, the processor(s) 110 is an electronic processor such as a microprocessor that is capable of performing various functions as described herein. In one embodiment, the handover system 170 includes a memory 210 that stores the driver assessment module 290, the operational condition adjustment module 291, and the transitioning module 292. The memory 210 is a random-access memory (RAM), read-only memory (ROM), a hard disk drive, a flash memory, or other suitable memory for storing the modules 290, 291, and 292. The modules 290, 291, and 292 are, for example, computer-readable instructions that when executed by the processor(s) 110 cause the processor(s) 110 to perform the various functions disclosed herein.

Furthermore, in one embodiment, the handover system 170 includes a data store 240. The data store 240 is, in one embodiment, an electronic data structure such as a database that is stored in the memory 210 or another memory and that is configured with routines that can be executed by the processor(s) 110 for analyzing stored data, providing stored data, organizing stored data, and so on. Thus, in one embodiment, the data store 240 stores data used by the modules 290, 291, and 292 in executing various functions. In one embodiment, the data store 240 includes sensor data 250, ability level data 260 and comfort level data 270 along with, for example, other information that is used by the modules 290, 291, and 292. The sensor data 250 may include some or all of the sensor data 119 shown in FIG. 1 and described later in this disclosure. The ability level data 260 may include data related to the ability level of the driver, while the comfort level data 270 may include data related to the comfort level of the driver. Both the ability level and comfort level of the driver will be described later in this disclosure.

Accordingly, the driver assessment module 290 generally includes instructions that function to control the processor(s) 110 to determine an ability level and a comfort level of a driver of the vehicle 100. The comfort level of the driver may be based on a learned physiological condition of the driver determined by observing one or more physiological conditions of the driver when the driver operates the vehicle in the driver input mode.

In one example, the comfort level of the driver is determined by the driver assessment module 290 by taking one or more physiological measurements of the driver as the driver operates the vehicle 100 in a driver input mode. As stated before, the driver input mode is a mode in which the operation of the vehicle 100 depends at least in part on inputs provided by the driver. In addition to physiological based information, the comfort level can be learned from vehicle data with the need for physiological data. In particular, the comfort level may be determined by statistically observing a particular driver's vehicle data over time and determine what they are comfortable with using machine learning and some statistical inference.

The physiological measurements of the driver may be performed by the physiological sensor system 180 and the sensors 181-185 that make up the physiological sensor system 180. As such, the physiological measurements may include the pulse or heart rate of the driver taken by the heart rate sensor 181, the body temperature of the driver taken by the body temperature sensor 182, the respiration rate of the driver taken by the respiration sensor 183, the oxygen saturation of the blood of the driver taken by the oxygen saturation sensor 184, and/or visual physiological measurements taken by the camera 185 which has a field of view that includes the driver as the driver operates the vehicle 100 in the driver input mode. The physiological measurements taken by the camera 185 could include things regarding the perspiration of the driver, the facial expression and/or eye movements of the driver, and/or any gestures made by the driver.

The physiological measurements mentioned above may be combined into a physiological profile of the driver. The physiological measurements making up the profile may be an overall average of each of the measurements or can be provided on a grading system. As such, the physiological measurements could be weighed against each other to determine an overall comfort level that the driver usually exudes when operating the vehicle 100 in the driver input mode. So, if the body temperature of the driver is extremely high, but the pulse of the driver is at a typical average, this may indicate that while the pulse of the driver is acceptable, the high body temperature of the driver could indicate that the driver is sick or under significant stress. As such, the comfort profile developed can consider any of the physiological measurements performed by the sensors 181-185 of the physiological sensor system 180 and then weighted accordingly to determine an overall comfort level of the driver. In some situations, one or more measurements taken by the sensors 181-185 may be so heavily weighted and so severe that they essentially trump the other readings. For example, if the heart rate sensor 181 collects data that is determined to be indicative of the heart attack, the comfort level of the driver may be significantly impacted such that changing the vehicle 100 from the autonomous mode to the driver input mode is either not possible or not advisable. In such cases, as will be explained later in this disclosure, the vehicle 100 may be placed in a safe operating mode. In one example, the safe operating mode of the vehicle 100 may be a mode where the vehicle 100 is parked.

In addition to physiological based information, the comfort level can be learned from vehicle data with the need for physiological data. In particular, the comfort level may be determined by statistically observing a particular driver's vehicle data over time and determine what they are comfortable with using machine learning and some statistical inference.

As to the ability level, in one example, the ability level of the driver may be determined by processing information generated by the vehicle sensors 121. As stated before, the vehicle sensors 121 could include any one of a number of different sensors, such as speed sensors, wheel slip sensors, accelerometers, inertial motion sensors, gyroscopes, and the like. As such, the sensors may be able to determine the overall forces acting on the vehicle 100, and by way of extension, the driver while the driver operates the vehicle 100 in a driver input mode.

For example, if it is determined that a driver is generally able to operate the vehicle at a higher rate of speed than another driver, it may be determined that the first driver has a greater driver ability level. Additionally, the driver assessment module 290 could look at the overall driving habits of the driver under emergency situations, such as sudden braking situations, wherein vehicles or objects suddenly slow down or are suddenly placed in front of the vehicle 100. Based on the overall reaction time of the driver, the driver assessment module 290 can again determine the overall ability level of the driver. So, as an example, if the driver assessment module 290 determines that the driver has a fairly fast reaction time, the driver assessment module may determine that the ability of the driver is high as in comparison to a driver that has a fairly slow reaction time.

In addition to observing sensors 121 as the driver operates the vehicle 100 in the driver input mode, the driver assessment module 290 could also use driver information in order to determine the overall ability of the driver. This driver information could include such things like age, years being a licensed driver, total miles driven, number of accidents, accidents that were the fault of the driver, occupation, number of hours the driver slept the night before, body mass index, and other information that may in some way impact the overall ability of the driver.

Using the information described above, the driver assessment module 290 is able to determine a driver comfort level in a driver ability level. This determination may be made by using artificial intelligence algorithms, neural networks, and/or machine learning algorithms to determine and update the comfort level in the driver ability level as new data is collected and evaluated. Data related to the driver ability level may be stored in the data store 240 as ability level data 260. Data related to the comfort level of the driver may be stored in the data store 240 as comfort level data 270.

The operational condition adjustment module 291 when executed by the processor(s) 110 cause the processor(s) 110 to adjust at least one operating condition of the vehicle 100 to be within the ability level of the driver and comfort level of the driver in response to the handover event. Essentially, the operational condition adjustment module 291 can change one or more operating conditions of the vehicle 100 by utilizing one or more actuators 150. These actuators 150, as will be described later in this disclosure, may be able to control multiple vehicle systems that relate to the movement of the vehicle 100. These vehicle systems may include vehicle steering systems, throttle systems, braking systems, or any other system related to the movement of the vehicle 100. Additionally, the vehicle systems may also include systems outside of those systems that relate to the movement of the vehicle 100. For example, the operational condition adjustment module 291 may adjust the heating ventilation and air conditioning settings to provide a more comfortable environment for the driver in an effort to improve the overall comfort level of the driver.

The handover event can be any event either in the present time or future time that requires or prefers input from the driver to control the vehicle 100. As stated before, the handover event could include events such as the failure of one or more vehicle systems and/or sensors. The events could also include external actions acting upon the vehicle 100, such as inclement weather that may impact the ability of one or more vehicle systems and/or sensors to operate in such a way so as to allow the autonomous operation of the vehicle 100. The events could also include situations where in the vehicle 100 is operating in an area where the autonomous control the vehicle may result in an unsafe situation. This type of situation could be a situation wherein the environment in which the vehicle 100 is operating and is undergoing change caused by events such as road construction, natural disasters, and the like. This type of situation could also include situations wherein the vehicle 100 is operating in an area outside of the preferred autonomous area, such as a country road, residential neighborhood, driveway, or in an off-road environment.

The transitioning module 292 when executed by the processor(s) 110 cause the processor(s) 110 to transition the vehicle 100 from the autonomous mode to a driver input mode after the operating condition of the vehicle 100 has been adjusted to be within the ability level of the driver and the comfort level of the driver. Once this is completed, the vehicle 100 has been changed from the autonomous mode to the driver input mode and requires input from the driver.

The transitioning module 292 may include further instructions that when executed by the processor(s) 110 causes the processor(s) 110 to determine a transition window for transitioning the vehicle from the autonomous mode to the driver input mode. The transition window may be an amount of time in which the vehicle 100 should be transitioned from the autonomous mode to the driver input mode. For example, if the autonomous system is only able to operate the vehicle 100 in an autonomous mode when on an expressway, the transition window may be the amount of time before the vehicle 100 exits the expressway and therefore needs to change from the autonomous mode to the driver input mode.

The transitioning module 292 may also cause the processor(s) 110 to determine an adjustment window. The adjustment window is a time duration for adjusting the operating condition of the vehicle 100 so that the operating condition of the vehicle 100 is within the ability level and/or comfort level of the driver. For example, if the ability level of the driver indicates that the driver is only able to operate the vehicle under 65 mph and the vehicle is traveling at a greater speed than 65 mph, the adjustment window would be the amount of time it takes for slowing the vehicle down from 100 mph to 65 mph. The same could be true for the comfort level of the driver. If the comfort level of the driver indicates that the driver is under stress, such as a high pulse or is indicated as being asleep, the adjustment window could include the time duration for reducing the pulse of the driver and/or waking the driver up from sleep.

The transitioning module 292 may also cause the processor(s) 110 to determine if the adjustment window is outside the transition window. For example, if the vehicle 100 is changed from the autonomous mode to the driver input mode within a two minute window and the adjustment window is three minutes, the comfort level and/or ability level of the driver will not be within the appropriate range before the required change from the autonomous mode to the driver input mode. If such a situation arises, the transitioning module 292 may make any one of a number of different choices.

In one situation, the transition module 292 will next determine if at least the ability level of the driver will be such that the vehicle 100 can be transitioned from the autonomous mode to the driver input mode. Essentially, in this situation, the transitioning module 292 ignores the comfort level of the driver and then only looks at the ability level of the driver. In another situation, the transitioning module 292 may place the vehicle 100 in a safe operating mode. The safe operating mode of the vehicle 100 could be a mode wherein the vehicle is parked or is transitioned to an operational state wherein the vehicle 100 does not need to be changed from an autonomous mode to a driver input mode. In one example, instead of parking the vehicle 100, the speed of the vehicle 100 may be greatly reduced. In another example, the vehicle 100 may determine another route to take such that the vehicle 100 does not need to be changed from the autonomous mode to the driver input mode.

Figure 3:
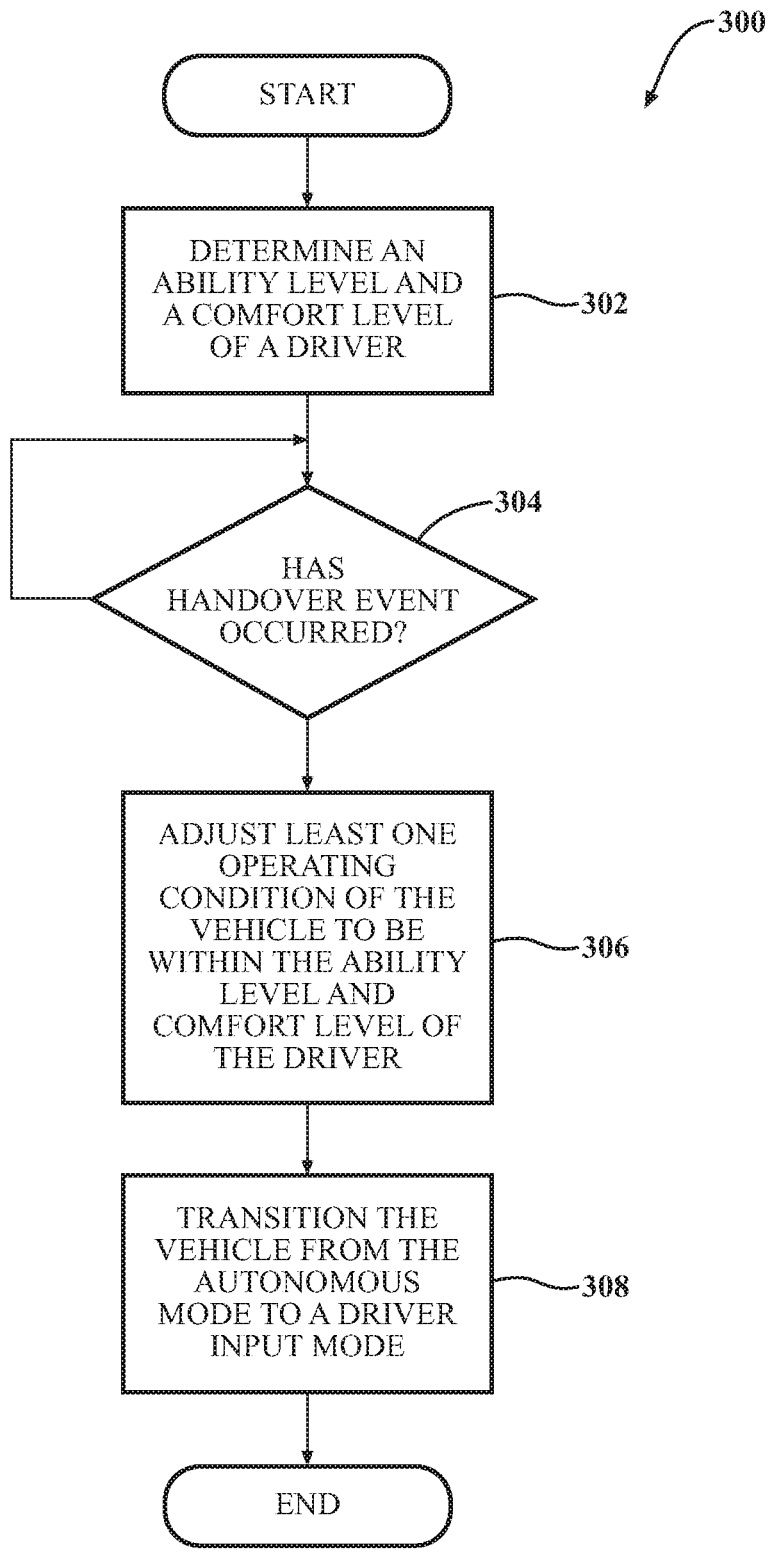
FIG. 3 illustrates a method for transitioning a vehicle from an autonomous mode in response to a handover event.

Referring to FIG. 3, a method 300 for transitioning a vehicle from an autonomous mode in response to a handover event is shown. The method 300 will be described from the viewpoint of the vehicle 100 of FIG. 1 and the handover system 170 of FIG. 2. However, it should be understood that this is just one example of implementing the method 300. While method 300 is discussed in combination with the handover system 170, it should be appreciated that the method 300 is not limited to being implemented within the handover system 170 but is instead one example of a system that may implement the method 300.

The method 300 begins at step 302, wherein the driver assessment module 290 causes the processor(s) 110 of the vehicle 100 to determine an ability level and a comfort level of the driver. As stated in more detail in the paragraphs above, the ability level of the driver is the outer limits of the ability of the driver to safely operate the vehicle 100. The ability level of the driver may be determined by monitoring one or more vehicle sensors 121 to determine how the driver operates the vehicle in the driver input mode. In addition to using information from the one or more vehicle sensors 121, information regarding the driver may also be utilized, such as age, occupation, body mass index, or other information about the driver. This information is then evaluated and an overall driver ability level is determined.

As stated in more detail in the paragraphs above, the comfort level is the overall comfort that the driver exhibits when operating the vehicle 100 in the driver input mode Like before, the comfort level may be based by observing and taking measurements by the sensors 181-185 making up the physiological sensor system 180. Using the information described above, the driver assessment module 290 is able to determine a driver comfort level and a driver ability level. This determination may be made by using artificial intelligence algorithms, neural networks, and/or machine learning algorithms to determine and update the comfort level and the driver ability level as new data is collected and evaluated. In addition to physiological based information, the comfort level can be learned from vehicle data with the need for physiological data. In particular, the comfort level may be determined by statistically observing a particular driver's vehicle data over time and determine what they are comfortable with using machine learning and some statistical inference.

In step 304, the method 300 determines if a handover event has occurred. As described in greater detail above, the handover event could be a present or future event that results in the vehicle 100 utilizing input from the driver. As such, the vehicle 100 either immediately or sometime in the future will be required to change from an autonomous mode to a driver input mode. As stated in more detail before, the driver input event could be an event related to the failure of one or more systems or sensors of the vehicle 100, related to an external event such as inclement weather, or when the vehicle 100 will be operated in a location wherein the autonomous mode of the vehicle 100 will not be able to safely operate the vehicle 100. It should be understood that the handover event could be any event that requires the eventual input from a driver to operate the vehicle 100.

If it is determined that a handover event has occurred, the method 300 proceeds to step 306. At step 306, the operational condition adjustment module 291 causes the processor(s) 110 to adjust the operating condition of the vehicle 100, such that the operating condition of the vehicle 100 is within the ability level and/or comfort level of the driver. In this situation, the operational conditional adjustment module 291 may cause the processor(s) 110 to actuate one or more actuators 150 that may control the overall movement of the vehicle 100. In addition to controlling the movement of the vehicle 100, the actuators 150 may also control other vehicle systems to improve the comfort level of the driver.

After step 306 has been completed, the method proceeds to step 308, wherein the transition module 292 causes the processor(s) 110 to transition the vehicle 100 from the autonomous mode to the driver input mode. Once step 308 is completed, the vehicle 100 has been transitioned from the autonomous mode to the driver input mode and therefore requires at least some input from the driver.

Figure 4:
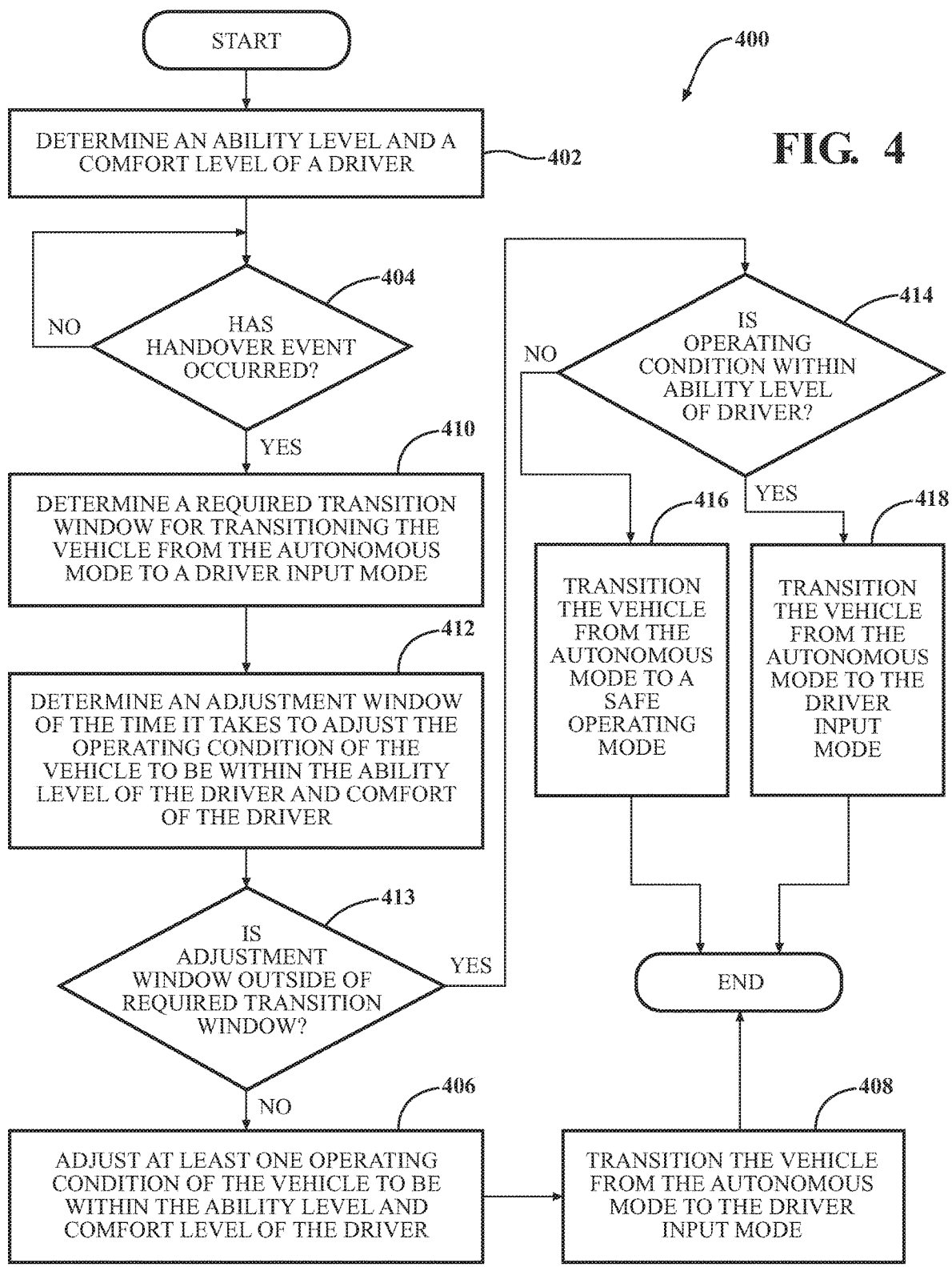
FIG. 4 illustrates another example of a method for transitioning a vehicle from an autonomous mode in response to a handover event.

Referring to FIG. 4, another method 400 for transitioning a vehicle from an autonomous mode in response to a handover event is shown. The method 400 will be described from the viewpoint of the vehicle 100 of FIG. 1 and the handover system 170 of FIG. 2. However, this is just one example of implementing the method 400. While the method 400 is discussed in combination with the handover system 170, it should be appreciated that the method 400 is not limited to being implemented within the handover system 170 but is instead one example of a system that may implement the method 400.

The method 400 begins at step 402, wherein the driver assessment module 290 causes the processor(s) 110 to determine an ability level and a comfort level of the driver. The step 402 may be similar to the step 302 shown in FIG. 3 and described in the paragraphs above. In step 404, a determination is made if the handover event occurred. Similarly, step 404 may be similar to the step 304 shown in FIG. 3 and described in the paragraphs above.

If a handover event has occurred, the method 400 proceeds to step 410. In step 410, the transitioning module 292 causes the processor(s) 110 to determine a required transition window for transitioning the vehicle from the autonomous mode to a driver input mode. As explained in more detail before, the transition window may be an amount of time in which the vehicle 100 should be transitioned from the autonomous mode to the driver input mode.

In step 412, the transitioning module 292 causes the processor(s) 110 to determine an adjustment window. As stated in more detail before, the adjustment window is a time duration for adjusting the operating condition of the vehicle 100 so that the operating condition of the vehicle 100 is within the ability level and/or comfort level of the driver.

In step 413, the transitioning module 292 causes the processor(s) 110 to decide if the adjustment window is outside the required transition window. As explained before, if the vehicle 100 should be changed from the autonomous mode to the driver input mode within a two minute window and the adjustment window is three minutes, the comfort level and/or ability level of the driver will not be within the appropriate range before the required change from the autonomous mode to the driver input mode.

If a determination is made that the adjustment window is not outside the required transition window, the method 400 will proceed to step 406, wherein the operational condition adjustment module 291 causes the processor(s) 110 to adjust at least one operating condition of the vehicle to be within the ability level and comfort level of the driver. Step 406 is similar to step 306, shown in FIG. 3 and described in the paragraphs above. After step 406 is completed, the method proceeds to step 408, wherein the transitioning module 292 causes the processor(s) 110 to transition the vehicle 100 from the autonomous mode to the driver input mode. Step 408 may be similar to step 308, shown in FIG. 3 and described in the paragraphs above.

Returning to step 413, if a determination is made that the adjustment window is outside the required transition window, the method 400 proceeds to step 414. In step 414, the transitioning module 292 causes the processor(s) 110 to decide if the operating condition of the vehicle 100 is within the ability level of the driver. In this example, the method 400 may ignore the comfort level of the driver and decide if at least the ability level of the driver is within the operating condition of the vehicle 100.

If the operating condition of the vehicle 100 is within the ability level of the driver, the method 400 proceeds to step 418, wherein the transitioning module 292 causes the processor(s) 110 to transition the vehicle 100 from the autonomous mode to the driver input mode. Conversely, if the operating condition of the vehicle 100 is not within the ability level of the driver, the method 400 proceeds to step 416, wherein the transitioning module 292 causes the processor(s) 110 to transition the vehicle 100 from the autonomous mode to a safe operating mode. The safe operating mode of the vehicle 100 could be a mode wherein the vehicle 100 is parked or is transitioned to an operational state wherein the vehicle 100 does not need to be changed from an autonomous mode to a driver input mode. In one example, instead of parking the vehicle 100, the speed of the vehicle 100 may be greatly reduced. In another example, the vehicle 100 may determine another route to take such that the vehicle 100 does not need to be changed from the autonomous mode to the driver input mode.

FIG. 1 will now be discussed in full detail as an example environment within which the system and methods disclosed herein may operate. In one or more embodiments, the vehicle 100 is an autonomous vehicle. As used herein, "autonomous vehicle" refers to a vehicle that operates in an autonomous mode. "Autonomous mode" refers to navigating and/or maneuvering the vehicle 100 along a travel route using one or more computing systems to control the vehicle 100 with minimal or no input from a human driver. In one or more embodiments, the vehicle 100 is highly automated or completely automated but may also change from the autonomous mode to a driver input mode, wherein the input from the driver is utilized to operate the vehicle safely.

The vehicle 100 can include processor(s) 110. In one or more arrangements, the processor(s) 110 can be a main processor of the vehicle 100. For instance, the processor(s) 110 can be an electronic control unit (ECU). The vehicle 100 can include one or more data stores 115 for storing one or more types of data. The data store 115 can include volatile and/or non-volatile memory. Examples of suitable data stores 115 include RAM (Random Access Memory), flash memory, ROM (Read Only Memory), PROM (Programmable Read-Only Memory), EPROM (Erasable Programmable Read-Only Memory), EEPROM (Electrically Erasable Programmable Read-Only Memory), registers, magnetic disks, optical disks, hard drives, or any other suitable storage medium, or any combination thereof. The data store 115 can be a component of the processor(s) 110, or the data store 115 can be operatively connected to the processor(s) 110 for use thereby. The term "operatively connected," as used throughout this description, can include direct or indirect connections, including connections without direct physical contact.

In one or more arrangements, the one or more data stores 115 can include map data 116. The map data 116 can include maps of one or more geographic areas. In some instances, the map data 116 can include information or data on roads, traffic control devices, road markings, structures, features, and/or landmarks in the one or more geographic areas. The map data 116 can be in any suitable form. In some instances, the map data 116 can include aerial views of an area. In some instances, the map data 116 can include ground views of an area, including 360-degree ground views. The map data 116 can include measurements, dimensions, distances, and/or information for one or more items included in the map data 116 and/or relative to other items included in the map data 116. The map data 116 can include a digital map with information about road geometry. The map data 116 can be high quality and/or highly detailed.

In one or more arrangements, the map data 116 can include one or more terrain maps 117. The terrain map(s) 117 can include information about the ground, terrain, roads, surfaces, and/or other features of one or more geographic areas. The terrain map(s) 117 can include elevation data in the one or more geographic areas. The map data 116 can be high quality and/or highly detailed. The terrain map(s) 117 can define one or more ground surfaces, which can include paved roads, unpaved roads, land, and other things that define a ground surface.

In one or more arrangements, the map data 116 can include one or more static obstacle maps 118. The static obstacle map(s) 118 can include information about one or more static obstacles located within one or more geographic areas. A "static obstacle" is a physical object whose position does not change or substantially change over a period of time and/or whose size does not change or substantially change over a period of time. Examples of static obstacles include trees, buildings, curbs, fences, railings, medians, utility poles, statues, monuments, signs, benches, furniture, mailboxes, large rocks, hills. The static obstacles can be objects that extend above ground level. The one or more static obstacles included in the static obstacle map(s) 118 can have location data, size data, dimension data, material data, and/or other data associated with it. The static obstacle map(s) 118 can include measurements, dimensions, distances, and/or information for one or more static obstacles. The static obstacle map(s) 118 can be high quality and/or highly detailed. The static obstacle map(s) 118 can be updated to reflect changes within a mapped area.

The one or more data stores 115 can include sensor data 119. In this context, "sensor data" means any information about the sensors that the vehicle 100 is equipped with, including the capabilities and other information about such sensors. As will be explained below, the vehicle 100 can include the sensor system 120. The sensor data 119 can relate to one or more sensors of the sensor system 120. As an example, in one or more arrangements, the sensor data 119 can include information on one or more LIDAR sensors 124 of the sensor system 120.

In some instances, at least a portion of the map data 116 and/or the sensor data 119 can be located in one or more data stores 115 located onboard the vehicle 100. Alternatively, or in addition, at least a portion of the map data 116 and/or the sensor data 119 can be located in one or more data stores 115 that are located remotely from the vehicle 100.

As noted above, the vehicle 100 can include the sensor system 120. The sensor system 120 can include one or more sensors. "Sensor" means any device, component and/or system that can detect, and/or sense something. The one or more sensors can be configured to detect, and/or sense in real-time. As used herein, the term "real-time" means a level of processing responsiveness that a user or system senses as sufficiently immediate for a particular process or determination to be made, or that enables the processor to keep up with some external process.

In arrangements in which the sensor system 120 includes a plurality of sensors, the sensors can work independently from each other. Alternatively, two or more of the sensors can work in combination with each other. In such a case, the two or more sensors can form a sensor network. The sensor system 120 and/or the one or more sensors can be operatively connected to the processor(s) 110, the data store(s) 115, and/or another element of the vehicle 100 (including any of the elements shown in FIG. 1). The sensor system 120 can acquire data of at least a portion of the external environment of the vehicle 100 (e.g., nearby vehicles).

The vehicle 100 can include an input system 130. An "input system" includes any device, component, system, element or arrangement or groups thereof that enable information/data to be entered into a machine. The input system 130 can receive an input from a vehicle passenger (e.g., a driver or a passenger). The vehicle 100 can include an output system 135. An "output system" includes any device, component, or arrangement or groups thereof that enable information/data to be presented to a vehicle passenger (e.g., a person, a vehicle passenger, etc.).

The vehicle 100 can include one or more vehicle systems 140. Various examples of the one or more vehicle systems 140 are shown in FIG. 1. However, the vehicle 100 can include more, fewer, or different vehicle systems. It should be appreciated that although particular vehicle systems are separately defined, each or any of the systems or portions thereof may be otherwise combined or segregated via hardware and/or software within the vehicle 100. The vehicle 100 can include a propulsion system 141, a braking system 142, a steering system 143, throttle system 144, a transmission system 145, a signaling system 146, and/or a navigation system 147. Each of these systems can include one or more devices, components, and/or a combination thereof, now known or later developed.

The navigation system 147 can include one or more devices, applications, and/or combinations thereof, now known or later developed, configured to determine the geographic location of the vehicle 100 and/or to determine a travel route for the vehicle 100. The navigation system 147 can include one or more mapping applications to determine a travel route for the vehicle 100. The navigation system 147 can include a global positioning system, a local positioning system or a geolocation system.

The processor(s) 110, the handover system 170, and/or the autonomous driving module(s) 160 can be operatively connected to communicate with the various vehicle systems 140 and/or individual components thereof. For example, returning to FIG. 1, the processor(s) 110 and/or the autonomous driving module(s) 160 can be in communication to send and/or receive information from the various vehicle systems 140 to control the movement, speed, maneuvering, heading, direction, etc. of the vehicle 100. The processor(s) 110, the handover system 170, and/or the autonomous driving module(s) 160 may control some or all of these vehicle systems 140 and, thus, may be partially or fully autonomous.

The processor(s) 110, the handover system 170, and/or the autonomous driving module(s) 160 can be operatively connected to communicate with the various vehicle systems 140 and/or individual components thereof. For example, returning to FIG. 1, the processor(s) 110, the handover system 170, and/or the autonomous driving module(s) 160 can be in communication to send and/or receive information from the various vehicle systems 140 to control the movement, speed, maneuvering, heading, direction, etc. of the vehicle 100. The processor(s) 110, the handover system 170, and/or the autonomous driving module(s) 160 may control some or all of these vehicle systems 140.

The processor(s) 110, the handover system 170, and/or the autonomous driving module(s) 160 may be operable to control the navigation and/or maneuvering of the vehicle 100 by controlling one or more of the vehicle systems 140 and/or components thereof. For instance, when operating in an autonomous mode, the processor(s) 110, the handover system 170, and/or the autonomous driving module(s) 160 can control the direction and/or speed of the vehicle 100. The processor(s) 110, the handover system 170, and/or the autonomous driving module(s) 160 can cause the vehicle 100 to accelerate (e.g., by increasing the supply of fuel provided to the engine), decelerate (e.g., by decreasing the supply of fuel to the engine and/or by applying brakes) and/or change direction (e.g., by turning the front two wheels). As used herein, "cause" or "causing" means to make, force, direct, command, instruct, and/or enable an event or action to occur or at least be in a state where such event or action may occur, either in a direct or indirect manner.

The vehicle 100 can include one or more actuators 150. The actuators 150 can be any element or combination of elements operable to modify, adjust and/or alter one or more of the vehicle systems 140 or components thereof to responsive to receiving signals or other inputs from the processor(s) 110 and/or the autonomous driving module(s) 160. Any suitable actuator can be used. For instance, the one or more actuators 150 can include motors, pneumatic actuators, hydraulic pistons, relays, solenoids, and/or piezoelectric actuators, just to name a few possibilities.

The vehicle 100 can include one or more modules, at least some of which are described herein. The modules can be implemented as computer-readable program code that, when executed by a processor(s) 110, implement one or more of the various processes described herein. One or more of the modules can be a component of the processor(s) 110, or one or more of the modules can be executed on and/or distributed among other processing systems to which the processor(s) 110 is operatively connected. The modules can include instructions (e.g., program logic) executable by one or more processor(s) 110. Alternatively, or in addition, one or more data store 115 may contain such instructions.

In one or more arrangements, one or more of the modules described herein can include artificial or computational intelligence elements, e.g., neural network, fuzzy logic or other machine learning algorithms. Further, in one or more arrangements, one or more of the modules can be distributed among a plurality of the modules described herein. In one or more arrangements, two or more of the modules described herein can be combined into a single module.

The vehicle 100 can include one or more autonomous driving modules 160. The autonomous driving module(s) 160 can be configured to receive data from the sensor system 120 and/or any other type of system capable of capturing information relating to the vehicle 100 and/or the external environment of the vehicle 100. In one or more arrangements, the autonomous driving module(s) 160 can use such data to generate one or more driving scene models. The autonomous driving module(s) 160 can determine position and velocity of the vehicle 100. The autonomous driving module(s) 160 can determine the location of obstacles, obstacles, or other environmental features including traffic signs, trees, shrubs, neighboring vehicles, pedestrians, etc.

The autonomous driving module(s) 160 can be configured to receive, and/or determine location information for obstacles within the external environment of the vehicle 100 for use by the processor(s) 110, and/or one or more of the modules described herein to estimate position and orientation of the vehicle 100, vehicle position in global coordinates based on signals from a plurality of satellites, or any other data and/or signals that could be used to determine the current state of the vehicle 100 or determine the position of the vehicle 100 with respect to its environment for use in either creating a map or determining the position of the vehicle 100 in respect to map data.

The autonomous driving module(s) 160 either independently or in combination with the handover system 170 can be configured to determine travel path(s), current autonomous driving maneuvers for the vehicle 100, future autonomous driving maneuvers and/or modifications to current autonomous driving maneuvers based on data acquired by the sensor system 120, driving scene models, and/or data from any other suitable source such as determinations from the sensor data 250. "Driving maneuver" means one or more actions that affect the movement of a vehicle. Examples of driving maneuvers include accelerating, decelerating, braking, turning, moving in a lateral direction of the vehicle 100, changing travel lanes, merging into a travel lane, and/or reversing, just to name a few possibilities. The autonomous driving module(s) 160 can be configured to implement determined driving maneuvers. The autonomous driving module(s) 160 can cause, directly or indirectly, such autonomous driving maneuvers to be implemented. As used herein, "cause" or "causing" means to make, command, instruct, and/or enable an event or action to occur or at least be in a state where such event or action may occur, either in a direct or indirect manner. The autonomous driving module(s) 160 can be configured to execute various vehicle functions and/or to transmit data to, receive data from, interact with, and/or control the vehicle 100 or one or more systems thereof (e.g., one or more of vehicle systems 140).

Detailed embodiments are disclosed herein. However, it is to be understood that the disclosed embodiments are intended only as examples. Therefore, specific structural and functional details disclosed herein are not to be interpreted as limiting, but merely as a basis for the claims and as a representative basis for teaching one skilled in the art to variously employ the aspects herein in virtually any appropriately detailed structure. Further, the terms and phrases used herein are not intended to be limiting but rather to provide an understandable description of possible implementations. Various embodiments are shown in FIGS. 1-4, but the embodiments are not limited to the illustrated structure or application.

The flowcharts and block diagrams in the figures illustrate the architecture, functionality, and operation of possible implementations of systems, methods, and computer program products according to various embodiments. In this regard, each block in the flowcharts or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved.

The systems, components and/or processes described above can be realized in hardware or a combination of hardware and software and can be realized in a centralized fashion in one processing system or in a distributed fashion where different elements are spread across several interconnected processing systems. Any kind of processing system or another apparatus adapted for carrying out the methods described herein is suited. A typical combination of hardware and software can be a processing system with computer-usable program code that, when being loaded and executed, controls the processing system such that it carries out the methods described herein. The systems, components and/or processes also can be embedded in a computer-readable storage, such as a computer program product or other data programs storage device, readable by a machine, tangibly embodying a program of instructions executable by the machine to perform methods and processes described herein. These elements also can be embedded in an application product which comprises all the features enabling the implementation of the methods described herein and, which when loaded in a processing system, is able to carry out these methods.

Furthermore, arrangements described herein may take the form of a computer program product embodied in one or more computer-readable media having computer-readable program code embodied, e.g., stored, thereon. Any combination of one or more computer-readable media may be utilized. The computer-readable medium may be a computer-readable signal medium or a computer-readable storage medium. The phrase "computer-readable storage medium" means a non-transitory storage medium. A computer-readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer-readable storage medium would include the following: a portable computer diskette, a hard disk drive (HDD), a solid-state drive (SSD), a read-only memory (ROM), an erasable programmable read-only memory (EPROM or Flash memory), a portable compact disc read-only memory (CD-ROM), a digital versatile disc (DVD), an optical storage device, a magnetic storage device, or any suitable combination of the foregoing. In the context of this document, a computer-readable storage medium may be any tangible medium that can contain or store a program for use by or in connection with an instruction execution system, apparatus, or device.

Generally, module as used herein includes routines, programs, objects, components, data structures, and so on that perform particular tasks or implement particular data types. In further aspects, a memory generally stores the noted modules. The memory associated with a module may be a buffer or cache embedded within a processor, a RAM, a ROM, a flash memory, or another suitable electronic storage medium. In still further aspects, a module as envisioned by the present disclosure is implemented as an application-specific integrated circuit (ASIC), a hardware component of a system on a chip (SoC), as a programmable logic array (PLA), or as another suitable hardware component that is embedded with a defined configuration set (e.g., instructions) for performing the disclosed functions.

Program code embodied on a computer-readable medium may be transmitted using any appropriate medium, including but not limited to wireless, wireline, optical fiber, cable, RF, etc., or any suitable combination of the foregoing. Computer program code for carrying out operations for aspects of the present arrangements may be written in any combination of one or more programming languages, including an object-oriented programming language such as Java™, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer, or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The terms "a" and "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The phrase "at least one of . . . and . . . " as used herein refers to and encompasses any and all possible combinations of one or more of the associated listed items. As an example, the phrase "at least one of A, B, and C" includes A only, B only, C only, or any combination thereof (e.g., AB, AC, BC or ABC).

Aspects herein can be embodied in other forms without departing from the spirit or essential attributes thereof. Accordingly, reference should be made to the following claims, rather than to the foregoing specification, as indicating the scope hereof.

What is claimed is:

1. A system for transitioning a vehicle from an autonomous mode in response to a handover event, the system comprising:
   one or more processors; and
   a memory device operably coupled with the one or more processors, the memory device storing instructions that, when executed by the one or more processors, cause the one or more processors to:
      determine an ability level and a comfort level of a driver of the vehicle, wherein the comfort level of the driver is based on a learned physiological condition of the driver determined by a neural network using machine learning and statistical inference by observing one or more physiological conditions of the driver over a time when the driver operates the vehicle in a driver input mode over the time,
      wherein the comfort level is measured by an overall comfort level obtained from a combination of weighted physiological measurements of the one or more physiological conditions of the driver over the time when the driver operates the vehicle in the driver input mode over the time, and wherein the ability level of the driver is based on an outer limit of an ability of the driver to operate the vehicle in the driver input mode;
      adjust at least one operating condition of the vehicle to be within the ability level of the driver and comfort level of the driver in response to the handover event;
      transition the vehicle from the autonomous mode to the driver input mode after the at least one operating condition of the vehicle has been adjusted to be within the ability level of the driver and the comfort level of the driver.

2. The system of claim 1, wherein the outer limit of the ability of the driver to operate the vehicle in the driver input mode is based on historical sensor information from the vehicle collected when the driver operates the vehicle in the driver input mode.

3. The system of claim 1, further comprising at least one physiological sensor operable coupled to the one or more processors, the at least one physiological sensor including at least one of a heart rate sensor configured to determine a pulse of the driver, a body temperature sensor configured to determine a body temperature of the driver, a respiration rate sensor configured to determine a respiration rate of the driver, an oxygen saturation sensor configured to determine a blood oxygen level of the driver, and a camera configured to observe an eye movement, gestures, or perspiration of the driver.

4. The system of claim 1, wherein the learned physiological condition of the driver is based on historical sensor information collected when the driver operates the vehicle in the driver input mode.

5. The system of claim 4, wherein the historical sensor information includes at least one of heart rate, perspiration rate, blood pressure, and gestures of the driver when the driver operates the vehicle in the driver input mode.

6. The system of claim 1, wherein the memory device further includes instructions that when executed by the one or more processors causes the one or more processors to:
determine a transition window for transitioning the vehicle from the autonomous mode to the driver input mode,
determine an adjustment window, wherein the adjustment window is a time duration for adjusting the at least one operating condition of the vehicle to be within the ability level of the driver and comfort of the driver, and
transition the vehicle to a safe operational mode when the adjustment window is outside the transition window.

7. The system of claim 6, wherein the safe operational mode includes at least one of bringing the vehicle to a stop and slowing the vehicle.

8. A method for transitioning a vehicle from an autonomous mode in response to a handover event occurs, the method comprising:
determining an ability level and a comfort level of a driver of the vehicle, wherein the comfort level of the driver is based on a learned physiological condition of the driver determined by a neural network using machine learning and statistical inference by observing one or more physiological conditions over a time of the driver when the driver operates the vehicle in a driver input mode over the time,
wherein the comfort level is measured by an overall comfort level obtained from a combination of weighted physiological measurements of the one or more physiological conditions of the driver over the time when the driver operates the vehicle in the driver input mode over the time, and
wherein the ability level of the driver is based on an outer limit of an ability of the driver to operate the vehicle in the driver input mode;
adjusting at least one operating condition of the vehicle to be within the ability level of the driver and comfort level in response to the handover event; and
transitioning the vehicle from the autonomous mode to the driver input mode after the at least one operating condition of the vehicle has been adjusted to be within the ability level of the driver and the comfort level of the driver.

9. The method of claim 8, wherein the ability level of the driver is based on an outer limit of an ability of the driver to operate the vehicle in the driver input mode.

10. The method of claim 9, wherein the outer limit of the ability of the driver to operate the vehicle in the driver input mode is based on historical sensor information from the vehicle collected when the driver operates the vehicle in the driver input mode.

11. The method of claim 8, wherein the learned physiological condition of the driver is based on historical sensor information collected when the driver operates the vehicle in the driver input mode.

12. The method of claim 11, wherein the historical sensor information includes at least one of heart rate, perspiration rate, blood pressure, and gestures of the driver when the driver operates the vehicle in the driver input mode.

13. The method of claim 8, further comprising:
determining a transition window for transitioning the vehicle from the autonomous mode to the driver input mode;
determining an adjustment window, wherein the adjustment window is a time duration for adjusting the at least one operating condition of the vehicle to be within the ability level of the driver and comfort of the driver; and
transitioning the vehicle to a safe operational mode when the adjustment window is outside the transition window.

14. The method of claim 13, wherein the safe operational mode includes at least one of bringing the vehicle to a stop and slowing the vehicle.

15. A non-transitory computer-readable medium for a vehicle from an autonomous mode when in response to a handover event and including instructions that when executed by one or more processors cause the one or more processors to:
determine an ability level and a comfort level of a driver of the vehicle, wherein the comfort level of the driver is based on a learned physiological condition of the driver determined by a neural network using machine learning and statistical inference by observing one or more physiological conditions of the driver over a time when the driver operates the vehicle in a driver input mode over the time,
wherein the comfort level is measured by an overall comfort level obtained from a combination of weighted physiological measurements of the one or more physiological conditions of the driver over the time when the driver operates the vehicle in the driver input mode over the time, and
wherein the ability level of the driver is based on an outer limit of an ability of the driver to operate the vehicle in the driver input mode;
adjust at least one operating condition of the vehicle to be within the ability level of the driver and comfort level of the driver in response to the handover event; and
transition the vehicle from the autonomous mode to the driver input mode after the at least one operating condition of the vehicle has been adjusted to be within the ability level of the driver and the comfort level of the driver.

16. The non-transitory computer-readable medium of claim 15, wherein the outer limit of the ability of the driver to operate the vehicle in the driver input mode is based on historical sensor information from the vehicle collected when the driver operates the vehicle in the driver input mode.

17. The non-transitory computer-readable medium of claim 15, wherein the learned physiological condition of the driver is based on historical sensor information collected when the driver operates the vehicle in the driver input mode.

18. The non-transitory computer-readable medium of claim 17, wherein the historical sensor information includes at least one of heart rate, perspiration rate, blood pressure, and gestures of the driver when the driver operates the vehicle in the driver input mode.

19. The non-transitory computer-readable medium of claim 15, further including instructions that when executed by one or more processors cause the one or more processors to:
  determine a transition window for transitioning the vehicle from the autonomous mode to the driver input mode;
  determine an adjustment window, wherein the adjustment window is a time duration for adjusting the at least one operating condition of the vehicle to be within the ability level of the driver and comfort of the driver; and
  transition the vehicle to a safe operational mode when adjustment window is outside the transition window.

20. The non-transitory computer-readable medium of claim 19, wherein the safe operational mode includes at least one of bringing the vehicle to a stop and slowing the vehicle.

* * * * *